United States Patent
Suzuki (10) Patent No.: US 8,608,663 B2
(45) Date of Patent: Dec. 17, 2013

(54) PULSE WAVE PERIOD MEASURING APPARATUS, PULSE WAVE PERIOD MEASURING METHOD, HEARTBEAT PERIOD MEASURING METHOD, AND RECORDING MEDIUM

(75) Inventor: Takuji Suzuki, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 1282 days.

(21) Appl. No.: 12/212,182

(22) Filed: Sep. 17, 2008

(65) Prior Publication Data

US 2009/0204011 A1    Aug. 13, 2009

(30) Foreign Application Priority Data

Feb. 12, 2008  (JP) .................................. 2008-30567

(51) Int. Cl.
  *A61B 5/02* (2006.01)
(52) U.S. Cl.
  USPC ............................. 600/500; 600/502; 600/508
(58) Field of Classification Search
  None
  See application file for complete search history.

(56) References Cited

U.S. PATENT DOCUMENTS

| 7,351,206 | B2 | 4/2008 | Suzuki et al. | |
| 2006/0189855 | A1 | 8/2006 | Moriya et al. | |
| 2006/0224074 | A1* | 10/2006 | Ouchi et al. | 600/513 |
| 2007/0106183 | A1 | 5/2007 | Suzuki et al. | |
| 2008/0004811 | A1 | 1/2008 | Suzuki et al. | |

FOREIGN PATENT DOCUMENTS

| JP | 1-126206 U | 8/1989 |
| JP | 2001-198094 | 7/2001 |
| JP | 2002-291710 | 10/2002 |
| JP | 2004-89314 | 3/2004 |
| JP | 2004-358022 | 12/2004 |
| JP | 2005-279113 | 10/2005 |
| JP | 2006-212218 | 8/2006 |
| JP | 2007-181628 | 7/2007 |
| JP | 2008-6005 | 1/2008 |

OTHER PUBLICATIONS

U.S. Appl. No. 12/167,586, filed Jul. 3, 2008, Ouchi, et al.
Office Action issued Jun. 26, 2012, in Japanese Patent Application No. 2008-030567 with English translation.

* cited by examiner

*Primary Examiner* — Benjamin P Blumel
(74) *Attorney, Agent, or Firm* — Oblon, Spivak, McClelland, Maier & Neustadt, L.L.P.

(57) ABSTRACT

A pulse wave period measuring apparatus according to an embodiment of the present invention detects a pulse wave of a subject, detects a maximum value and a minimum value in a predetermined period of the pulse wave, calculates one or more reference values between the maximum value and the minimum value in the predetermined period, based on one or more internally dividing ratios common to plural predetermined periods of the pulse wave, calculates two or more times in the predetermined period, the apparatus calculating the two or more times at which the pulse wave intersects with the one or more reference values, calculates a time period between each calculated time in the predetermined period and a corresponding calculated time in a last period before the predetermined period, as a pulse wave period of the pulse wave, calculates a variation of pulse wave periods, for two or more pulse wave periods calculated between the predetermined period and the last period before the predetermined period, and calculates, based on the variation of the pulse wave periods, the stability of measuring the pulse wave periods.

20 Claims, 10 Drawing Sheets

|  | PULSE WAVE AMPLITUDE | PEAK VALUE | RATIO |
|---|---|---|---|
| DATA 1 | 624 | 0 | 0 |
| DATA 2 | 416 | 140 | 0.336538 |
| DATA 3 | 507.6 | 43 | 0.084712 |
| DATA 4 | 281.9 | 45 | 0.159631 |
| DATA 5 | 464 | 26 | 0.056034 |
| DATA 6 | 618.1 | 184 | 0.297686 |
| DATA 7 | 436.9 | 91 | 0.208286 |
| DATA 8 | 343.6 | 127 | 0.369616 |
| DATA 9 | 548.7 | 203 | 0.369965 |
| DATA 10 | 510 | 158 | 0.309804 |
| DATA 11 | 621 | 271 | 0.436393 |
| DATA 12 | 252 | 120 | 0.47619 |
| DATA 13 | 684 | 403 | 0.589181 |
| DATA 14 | 822 | 524 | 0.63747 |
| DATA 15 | 562 | 332 | 0.590747 |

PULSE WAVE PERIOD MEASURING APPARATUS, PULSE WAVE PERIOD MEASURING METHOD, HEARTBEAT PERIOD MEASURING METHOD, AND RECORDING MEDIUM

CROSS REFERENCE TO RELATED APPLICATIONS

This application is based upon and claims the benefit of priority from the prior Japanese Patent Application No. 2008-30567, filed on Feb. 12, 2008, the entire contents of which are incorporated herein by reference.

BACKGROUND OF THE INVENTION

1. Field of the Invention

The present invention relates to a pulse wave period measuring apparatus, a pulse wave period measuring method, a heartbeat period measuring method, and a recording medium.

2. Background Art

A photoelectric pulse wave sensor is configured to measure a pulse wave by light. The sensor irradiates a light beam into a living body, and measures a reflected or transmitted light beam. When the light beam is irradiated into the living body, the light beam is absorbed by hemoglobin in the living body. Therefore, the intensity of the reflected or transmitted light beam varies according to the amount of blood. This implies that the intensity of the reflected or transmitted light beam varies synchronized with a heartbeat. Therefore, the photoelectric pulse wave sensor can measure a pulse wave of a subject by measuring the reflected or transmitted light beam. The sensor is used, for example, for monitoring a heart rate during exercise or the like.

The pulse wave is relatively easy to be measured, in comparison with other biological indicators such as an electrocardiograph. In general, the pulse wave sensor can be easily attached, and is suitable for use in daily life. On the other hand, the pulse wave often fluctuates greatly in amplitude and baseline, due to narrowing and ballooning of a blood vessel or a breathing disturbance. In addition, it has been known that a subject's motion causes a change in contact state between the sensor and the subject's body and a change of the internal blood flow in the subject's body, which greatly disturbs the waveform of the pulse wave. It is desirable to take account of the above-mentioned merits and demerits when the pulse wave is measured. It should be noted that a heart rate can be calculated by detecting a pulse wave period. The accuracy of detecting the pulse wave period is greatly affected by a distortion or deformation of the pulse wave. Therefore, it is required to provide methods of stably measuring the pulse wave and of determining whether or not the pulse wave is stably measured.

The pulse wave sensor is applicable, for example, to a device for easily monitoring, at home, a sleeping condition or a health condition during sleep. In recent years, significant efforts have been made to develop such a device. JP-A 2002-291710 (KOKAI) discloses a method which calculates a pulse beat period from the pulse wave measured during sleep, performs a frequency analysis on the pulse beat period, and determines the sleeping condition based on the analyzed result of the frequency analysis. More specifically, the method converts a series of pulse beat period data calculated from the pulse wave, into a frequency spectrum distribution, extracts a predetermined frequency band component from the frequency spectrum distribution, and determines the sleeping condition, based on the value obtained by integrating the frequency component.

However, the method disclosed in the JP-A 2002-291710 (KOKAI) has a problem that if noise is contained in the series of pulse beat period data, the noise has a significant effect on the frequency spectrum. Therefore, it is necessary to remove the noise contained in the pulse beat period, due to a distortion or deformation of the pulse wave.

Further, JP-A 2004-89314 (KOKAI) and JP-A 2001-198094 (KOKAI) disclose methods for detecting a distortion of a pulse waveform. The method disclosed in JP-A 2004-89314 (KOKAI) accumulates a reference waveform in advance, calculates a correlation value between the reference waveform and an observed waveform, and determines whether the observed waveform is normal or abnormal, based on the correlation value. The method disclosed in JP-A 2001-198094 (KOKAI) measures pulse wave periods for plural pulse beats, and determines whether an observed waveform is normal or abnormal, based on the variation of the pulse wave periods.

However, according to the method disclosed in JP-A 2004-89314 (KOKAI), when measuring each waveform, it is necessary to extract a waveform of a pulse beat and calculate a correlation between waveforms, so that the processing load is quite heavy. In particular, when processing is performed in the sensor, a high performance computer is required for the processing, and thus a larger computer is required. In addition, since increasing power consumption is expected for the processing, a larger battery is required. In this way, a larger sensor is required when the processing is performed in the sensor. Further, according to the method disclosed in JP-A 2001-198094 (KOKAI), since pulse wave periods for plural pulse beats are required, it takes too much time for the determination, and it is difficult to determine whether the waveform is normal or abnormal for each waveform. In fact, when a pulse wave is measured, it is often the case that only one waveform is abnormal due to a momentary motion or noise. However, the method cannot adequately deal with such a case. The methods disclosed in JP-A 2004-89314 (KOKAI) and JP-A 2001-198094 (KOKAI) have such problems.

SUMMARY OF THE INVENTION

An aspect of the present invention is, for example, a pulse wave period measuring apparatus including a pulse wave detecting unit configured to detect a pulse wave of a subject, a value detecting unit configured to detect a maximum value and a minimum value in a predetermined period of the pulse wave, a reference value calculating unit configured to calculate one or more reference values between the maximum value and the minimum value in the predetermined period, based on one or more internally dividing ratios common to plural predetermined periods of the pulse wave, a time calculating unit configured to calculate two or more times in the predetermined period, the time calculating unit calculating the two or more times at which the pulse wave intersects with the one or more reference values, a pulse wave period calculating unit configured to calculate a time period between each calculated time in the predetermined period and a corresponding calculated time in a last period before the predetermined period, as a pulse wave period of the pulse wave, a variation calculating unit configured to calculate a variation of pulse wave periods, for two or more pulse wave periods calculated between the predetermined period and the last period before the predetermined period, and a stability calculating unit configured to calculate, based on the variation of the pulse wave periods, the stability of measuring the pulse wave periods.

Another aspect of the present invention is, for example, a pulse wave period measuring method including detecting a pulse wave of a subject, detecting a maximum value and a minimum value in a predetermined period of the pulse wave, calculating one or more reference values between the maximum value and the minimum value in the predetermined period, based on one or more internally dividing ratios common to plural predetermined periods of the pulse wave, calculating two or more times in the predetermined period, the method calculating the two or more times at which the pulse wave intersects with the one or more reference values, calculating a time period between each calculated time in the predetermined period and a corresponding calculated time in a last period before the predetermined period, as a pulse wave period of the pulse wave, calculating a variation of pulse wave periods, for two or more pulse wave periods calculated between the predetermined period and the last period before the predetermined period, and calculating, based on the variation of the pulse wave periods, the stability of measuring the pulse wave periods.

Another aspect of the present invention is, for example, a computer readable recording medium which records a program causing a computer to execute a pulse wave period measuring method, the method including sampling pulse wave data from a pulse wave of a subject, detecting a maximum value and a minimum value in a predetermined period of the pulse wave, calculating one or more reference values between the maximum value and the minimum value in the predetermined period, based on one or more internally dividing ratios common to plural predetermined periods of the pulse wave, calculating two or more times in the predetermined period, the method calculating the two or more times at which the pulse wave intersects with the one or more reference values, calculating the time period between each calculated time in the predetermined period and a corresponding calculated time in a last period before the predetermined period, as a pulse wave period of the pulse wave, calculating a variation of pulse wave periods, for two or more pulse wave periods calculated between the predetermined period and the last period before the predetermined period, and calculating, based on the variation of the pulse wave periods, the stability of measuring the pulse wave periods.

Another aspect of the present invention is, for example, a heartbeat period measuring method including sampling heartbeat data from a heartbeat of a subject, detecting a maximum value and a minimum value in a predetermined period of the heartbeat, calculating one or more reference values between the maximum value and the minimum value in the predetermined period, based on one or more internally dividing ratios common to plural predetermined periods of the heartbeat, calculating two or more times in the predetermined period, the method calculating the two or more times at which the heartbeat intersects with the one or more reference values, calculating the time period between each calculated time in the predetermined period and a corresponding calculated time in a last period before the predetermined period, as a heartbeat period of the heartbeat, calculating a variation of heartbeat periods, for two or more heartbeat periods calculated between the predetermined period and the last period before the predetermined period, and calculating, based on the variation of the heartbeat periods, the stability of measuring the heartbeat periods.

DESCRIPTION OF THE INVENTION EMBODIMENTS

Embodiments of the present invention will be described with reference to the drawings.
(First Embodiment)

Figure 1:
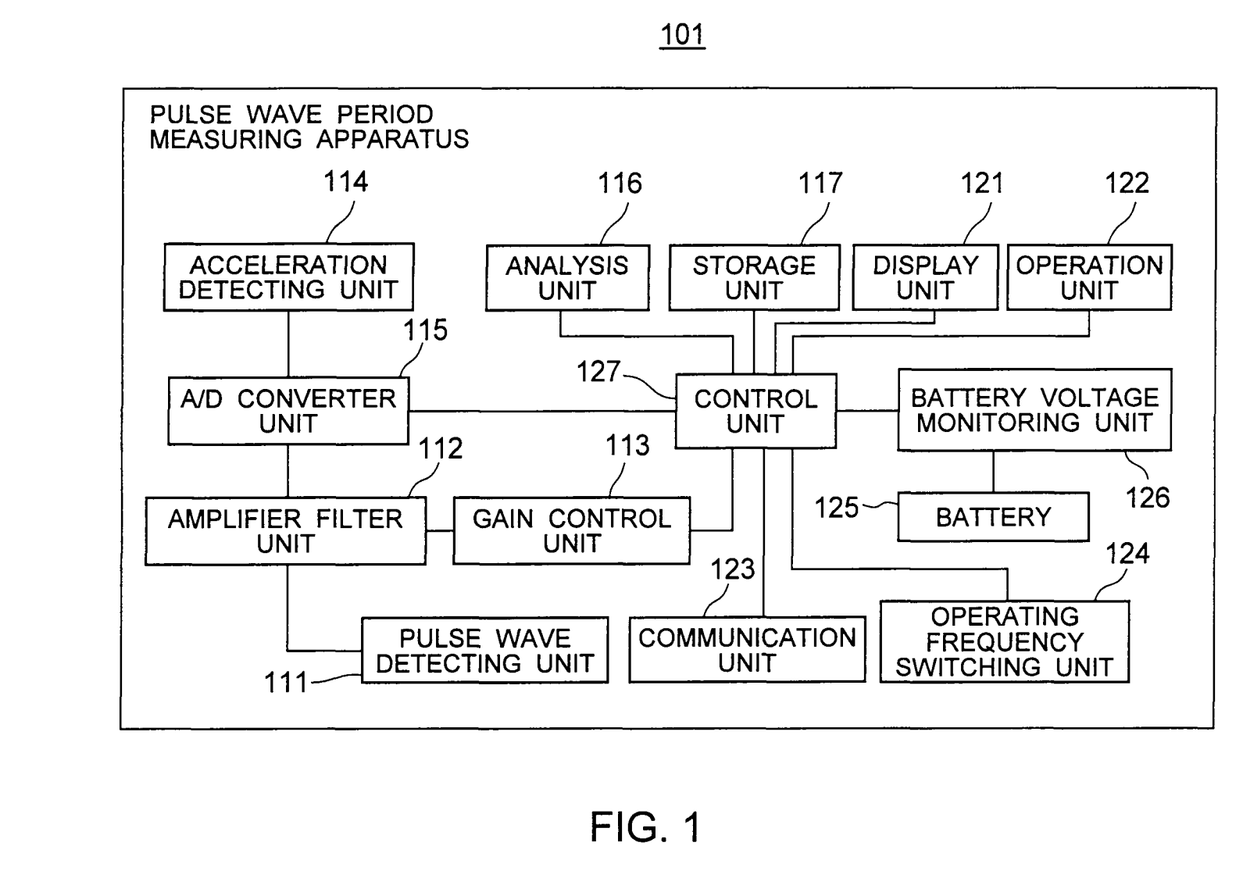
FIG. 1 is a functional block diagram of a pulse wave period measuring apparatus in accordance with a first embodiment.

FIG. 1 is a functional block diagram of a pulse wave period measuring apparatus 101 in accordance with a first embodiment. The apparatus 101 detects a pulse wave of a subject, and calculates a pulse wave period of the pulse wave. Furthermore, the apparatus 101 determines whether the pulse wave is normal or abnormal. The apparatus 101 stores the pulse wave period calculated from a normal pulse wave, as normal data, and stores the pulse wave period calculated from an abnormal pulse wave, as abnormal data.

Figure 2:
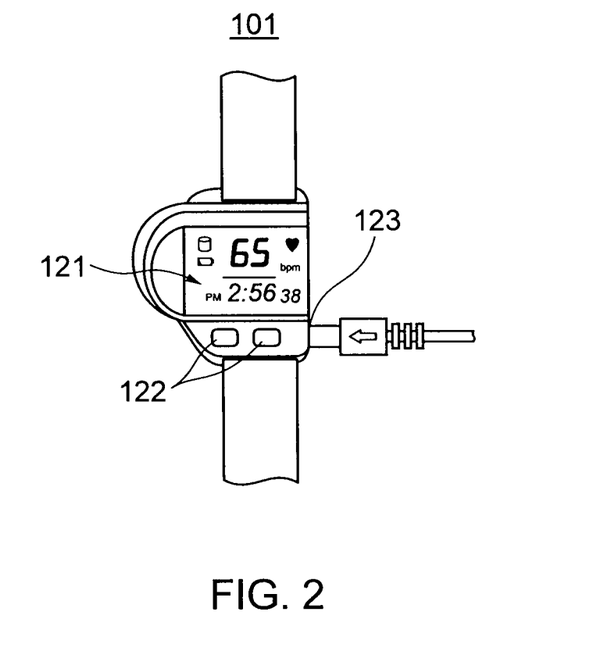
FIG. 2 is a front view of the pulse wave period measuring apparatus in FIG. 1.
Figure 3:
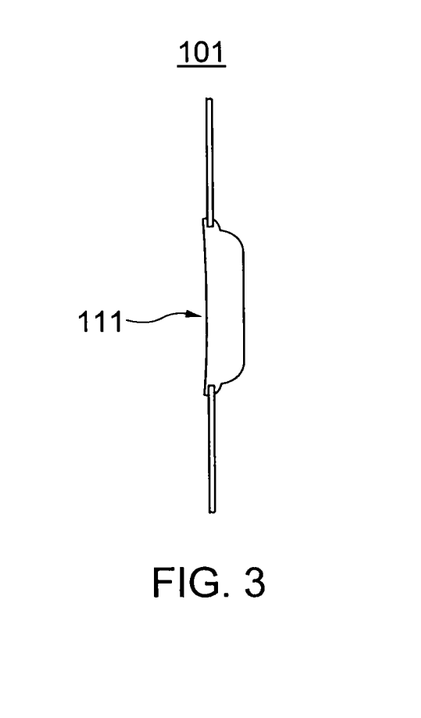
FIG. 3 is a side view of the pulse wave period measuring apparatus in FIG. 1.

FIG. 2 and FIG. 3 are a front view and a side view of the pulse wave period measuring apparatus 101 in FIG. 1. As shown in FIG. 2 and FIG. 3, the apparatus 101 in this embodiment is a wearable pulse wave sensor which is used while being worn on the wrist like a wrist watch. As shown in FIG. 2, the apparatus 101 is provided with a display unit 121, an operation unit 122, and a communication unit 123, in front of or on side of the apparatus 101. Further, as shown in FIG. 3, the apparatus 101 is provided with a pulse wave detecting unit 111 for detecting a pulse wave of a subject, on back side of the apparatus 101.

Returning to FIG. 1, the description will be continued.

The apparatus 101 in FIG. 1 is provided with the pulse wave detecting unit 111, an amplifier filter unit 112, a gain control unit 113, an acceleration detecting unit 114, an A/D (analogue/digital) converter unit 115, an analysis unit 116, a storage unit 117, the display unit 121, the operation unit 122, the communication unit 123, an operating frequency switching unit 124, a battery 125, a battery voltage monitoring unit 126, and a control unit 127.

The pulse wave detecting unit 111 is configured to detect a pulse wave of a subject. The pulse wave detecting unit 111 in this embodiment includes a green LED which emits a light beam toward the wrist, and a photodiode which measures a reflected light beam. The intensity of the reflected light varies in accordance with a change of a blood flow in a capillary blood vessel. The pulse wave detecting unit 111 can measure the pulse wave of the subject by measuring the reflected light. As described here, the pulse wave period measuring apparatus 101 in this embodiment is a photoelectric pulse wave sensor.

The amplifier filter unit 112 is configured to receive a pulse waveform detected by the pulse wave detecting unit 111, and amplify and filter the pulse waveform. The amplifier filter unit 112 in this embodiment includes a current/voltage converter which converts a current output from the photodiode into a voltage, an amplifier which amplifies the voltage, and high-pass and low-pass filters which filter the amplified voltage. The cutoff frequency of the high-pass filter is, for example, 0.1 Hz. The cutoff frequency of the low-pass filter is, for example, 50 Hz.

The gain control unit 113 is configured to control the gain of the amplifier filter unit 112, in accordance with a detected state of the pulse waveform. The gain control unit 113 in this embodiment calculates the amplitude of the pulse waveform input into the control unit 127, and controls the gain of the amplifier in accordance with the relation between the amplitude and a threshold.

The acceleration detecting unit 114 is configured to detect a dynamic acceleration which varies with a movement of the subject's wrist, and a static acceleration which varies depending on the subject's posture. The acceleration detecting unit 114 in this embodiment is an acceleration sensor which can detect acceleration from −2 g to +2 g in the three-axial directions, and is installed in the main body of the pulse wave period measuring apparatus 101.

The A/D converter unit 115 is configured to perform A/D conversion on the pulse waveform detected by the pulse wave detecting unit 111 and on an acceleration waveform detected by the acceleration detecting unit 114. The pulse waveform in this embodiment is detected by the pulse wave detecting unit 111, amplified and filtered by the amplifier filter unit 112, and converted by the A/D converter unit 115. The acceleration waveform in this embodiment is detected by the acceleration detecting unit 114, and converted by the A/D converter unit 115.

The analysis unit 116 is configured to receive the pulse waveform and the acceleration waveform converted by the A/D conversion, and analyze the pulse waveform and the acceleration waveform. For example, the analysis unit 116 analyzes the acceleration waveform, and performs a body motion calculation process of calculating body motion data of the subject. Further, the analysis unit 116 analyzes the calculated body motion data, and performs an awake/asleep determination process of determining whether the subject is awake or asleep. Further, the analysis unit 116 analyzes the pulse waveform, and performs a pulse wave period calculation process of calculating pulse wave period data of the pulse wave.

The storage unit 117 is configured to store various data derived by the analysis unit 116. The storage unit 117 stores the body motion data calculated by the body motion calculation process, a determined result and sleeping time data obtained by the awake/asleep determination process, the pulse wave period data calculated by the pulse wave period calculation process, and the like. The storage unit 117 is, for example, a flash memory.

Now, the body motion calculation process will be described.

Figure 4:
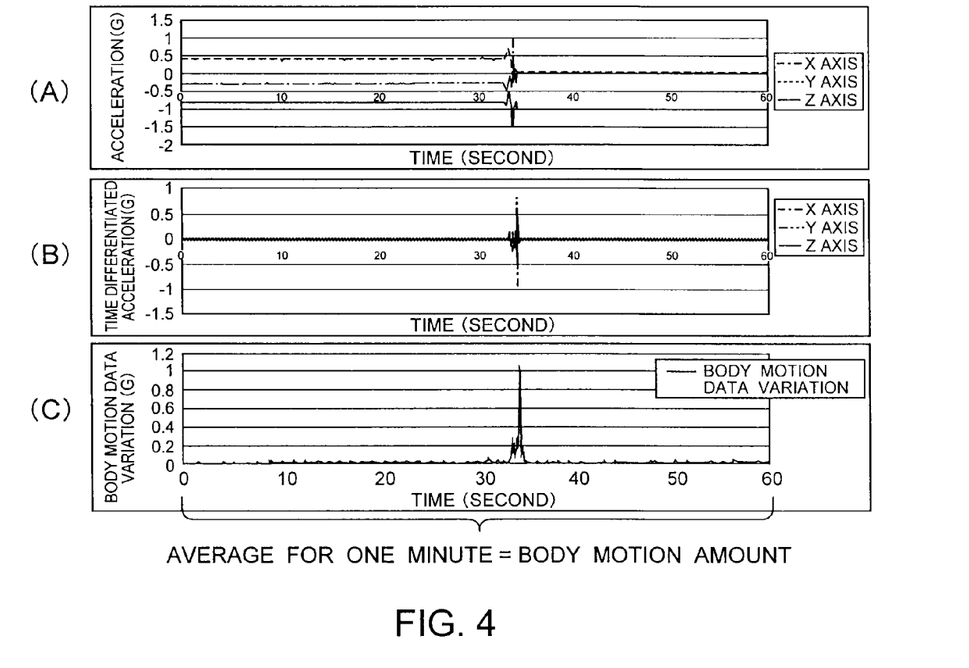
FIG. 4 is a drawing for explaining a body motion calculation process.

First, the analysis unit 116 obtains acceleration data in the three-axial directions. An example of the acceleration data is shown in FIG. 4A. Next, the analysis unit 116 performs time differentiation on the acceleration data to derive differential coefficients in the three-axial directions. An example of the differential coefficients is shown in FIG. 4B. Next, the analysis unit 116 calculates a body motion data variation which is the norm of the differential coefficients. An example of the body motion data variation is shown in FIG. 4C. Finally, the analysis unit 116 calculates a body motion amount which is the average of the body motion data variation for a predetermined time period. The predetermined time period is, for example, one minute.

Subsequently, the awake/asleep determination process will be described.

First, the analysis unit 116 performs a body motion determination. In the body motion determination, the analysis unit 116 compares the body motion data variation with a threshold (body motion threshold). If the body motion data variation is greater than the threshold, the analysis unit 116 determines that a body motion occurred. The body motion threshold is, for example, 0.01 G. Next, the analysis unit 116 performs an awake/asleep determination. In the awake/asleep determination, the analysis unit 116 compares the frequency of body motion occurrences with a threshold (frequency threshold). If the frequency of body motion occurrences is equal to or greater than the threshold, the analysis unit 116 determines that the body motion occurred during waking, and if the frequency of body motion occurrences is less than the threshold, the analysis unit 116 determines that the body motion occurred during sleeping. Alternatively, the analysis unit 116 may determine that the body motion occurred during sleeping, if the frequency of body motion occurrences is equal to or greater than the threshold, and the pulse wave period is longer than the average of the past pulse wave periods during sleeping. The frequency threshold is, for example, five times per minute.

Figure 5:
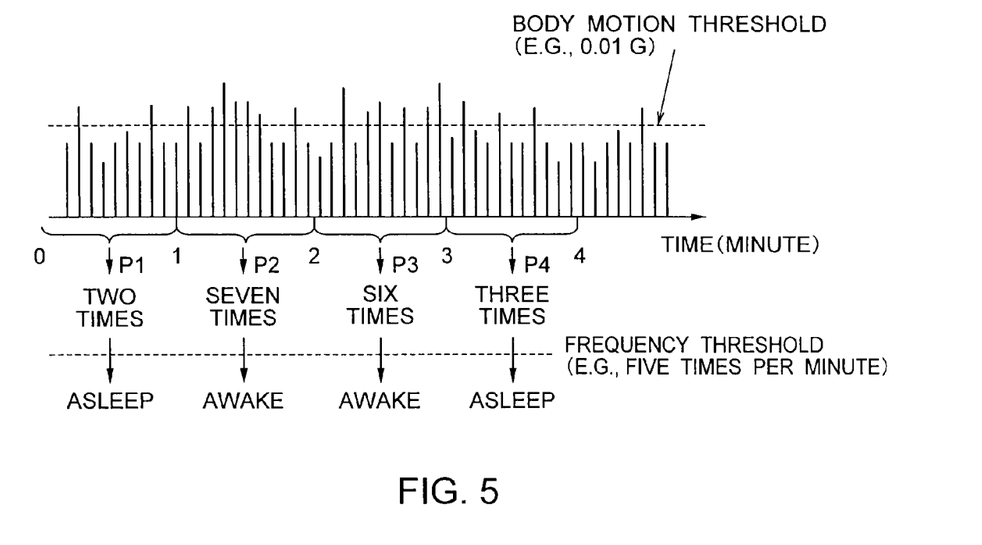
FIG. 5 is a drawing for explaining an awake/asleep determination process.

The awake/asleep determination process is schematically shown in FIG. 5. FIG. 5 shows four periods P1, P2, P3, and P4, a body motion threshold 0.01 G, and a frequency threshold "five times per minute". The frequencies of body motion occurrences in the periods P1, P2, P3, and P4 are two times, seven times, six times, and three times respectively. Therefore, body motions in the periods P1, P2, P3, and P4 are determined as motions during sleeping, motions during waking, motions during waking, and motions during sleeping respectively. In this case, the transition time from awake to asleep is detected as an initiation time, and the transition time from asleep to awake is detected as a termination time. Furthermore, sleeping time is calculated by calculating the difference between the initiation time and the termination time.

If there is no need to determine whether the subject is awake or asleep, neither the body motion calculation process nor the awake/asleep determination process is required. In this case, the analysis unit 116 performs only the pulse wave period calculation process of the above three processes. The pulse wave period calculation process will be described later.

Returning to FIG. 1, the description will be continued.

The display unit 121 is an output user interface. The display unit 121 displays, for example, time, sleeping time, pulse rate, pulse wave measuring state, battery state, memory state, communication state, and the like. The display unit 121 is, for example, an LCD (Liquid Crystal Display).

The operation unit 122 is an input user interface. The operation unit 122 is provided with, for example, a mode switching button for switching between a time mode and a measurement mode, a back light button for turning on a back light, and the like.

The communication unit 123 is an interface to communicate with an external device. The communication unit 123 is, for example, a USB port. Examples of the external device include a PC, a PDA terminal, a cell phone, and the like. The communication unit 123 allows a measured result of the pulse wave to be saved in an HDD of the PC or to be analyzed by analysis software in the PC.

The operating frequency switching unit 124 is configured to switch the operating frequency depending on the operating mode. When the operating mode is switched using the operation unit 122, the operating frequency switching unit 124 switches the operating frequency.

The battery 125 is a power source of the pulse wave period measuring apparatus 101.

The battery voltage monitoring unit 126 is configured to monitor the voltage of the battery 125.

The control unit 127 is configured to control the pulse wave period measuring apparatus 101. For example, the control unit 127 sends a processing request to a functional block, in response to an instruction from the operation unit 122. Examples of the instruction include the start of measurement, the end of measurement, the power ON/OFF, and the like.

Figure 6:
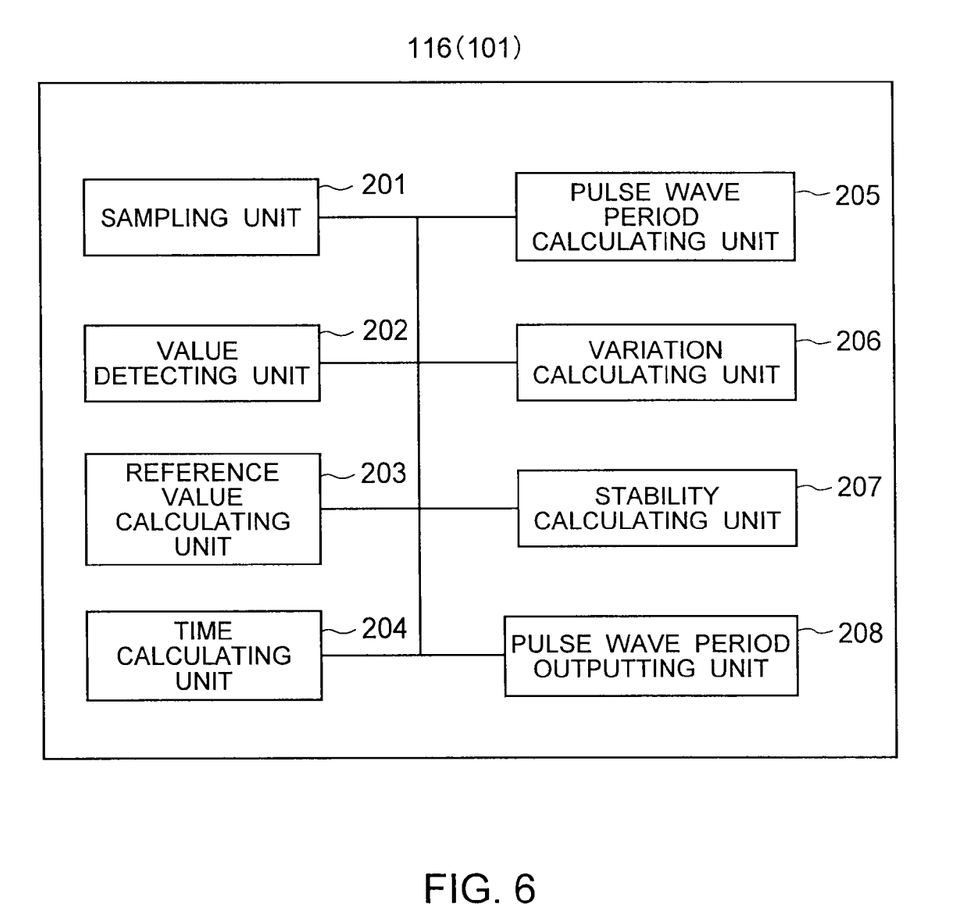
FIG. 6 is a functional block diagram showing functional blocks regarding a pulse wave period calculation process.
Figure 7:
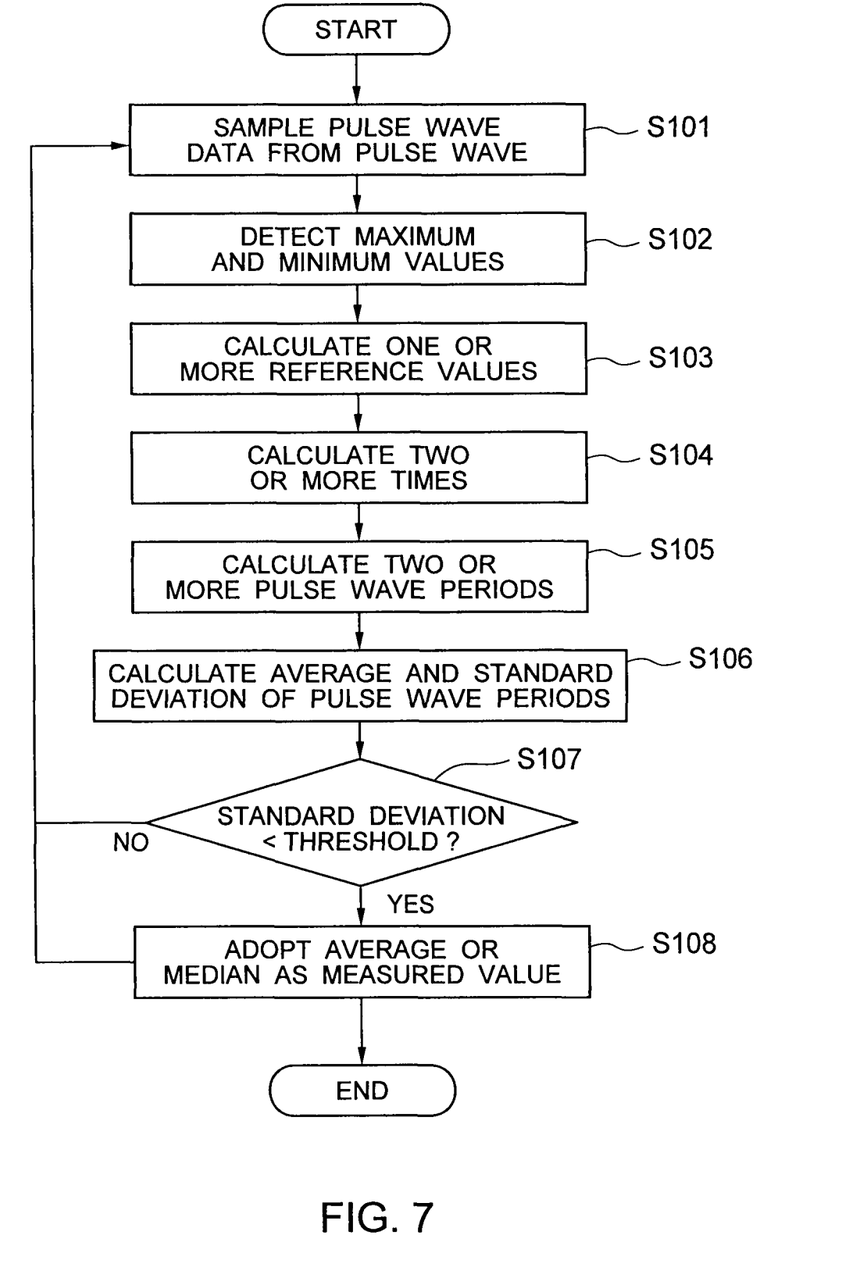
FIG. 7 is a flowchart regarding the pulse wave period calculation process.

Now, the pulse wave period calculation process performed by the analysis unit 116 will be described. FIG. 6 is a functional block diagram showing functional blocks regarding the pulse wave period calculation process. FIG. 7 is a flowchart regarding the pulse wave period calculation process.

As shown in FIG. 6, the analysis unit 116 includes a sampling unit 201, a value detecting unit 202, a reference value calculating unit 203, a time calculating unit 204, a pulse wave period calculating unit 205, a variation calculating unit 206, a stability calculating unit 207, and a pulse wave period outputting unit 208. Details of these functional blocks will be described with reference to the flowchart in FIG. 7. The flowchart in FIG. 7 will be described hereinafter.

Figure 8:
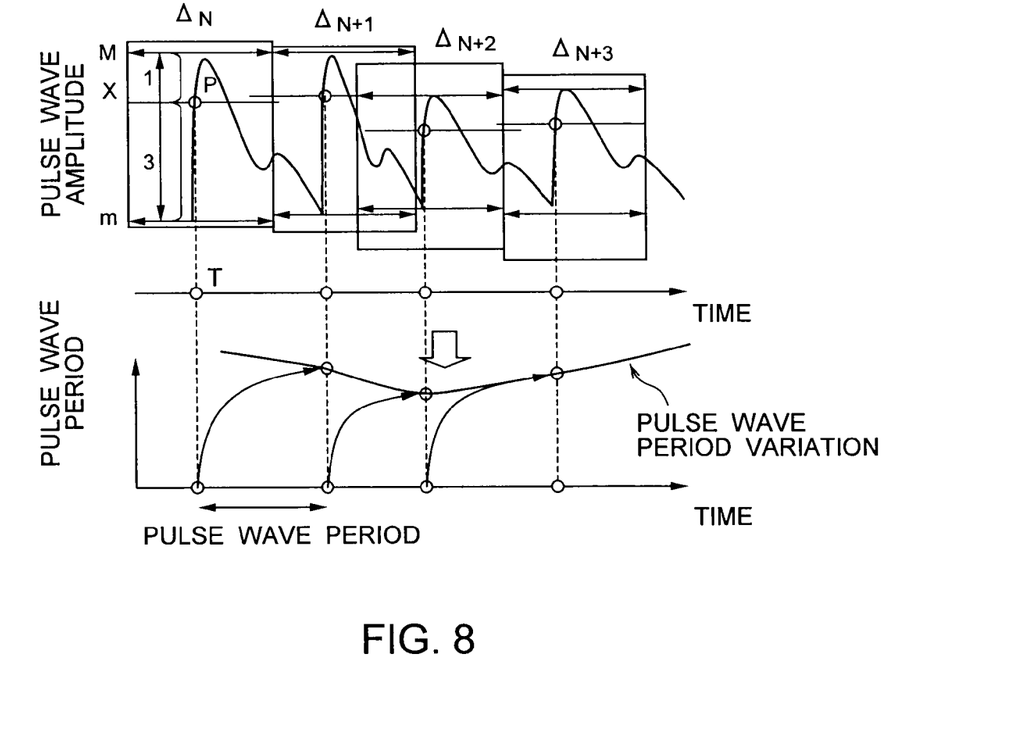
FIG. 8 is a drawing for explaining the pulse wave period calculation process.

First, the sampling unit 201 samples pulse wave data from the pulse wave (S101). Next, the value detecting unit 202 detects a maximum value and a minimum value in a predetermined period of the pulse wave (S102). FIG. 8 shows a maximum value "M" and a minimum value "m" in a predetermined period "AN" of the pulse wave. The predetermined period in this embodiment is an about-one-second period whose center is at a predetermined sampling point. The maximum value and the minimum value in this embodiment are obtained from a series of pulse wave data sampled in the predetermined period.

Figure 9:
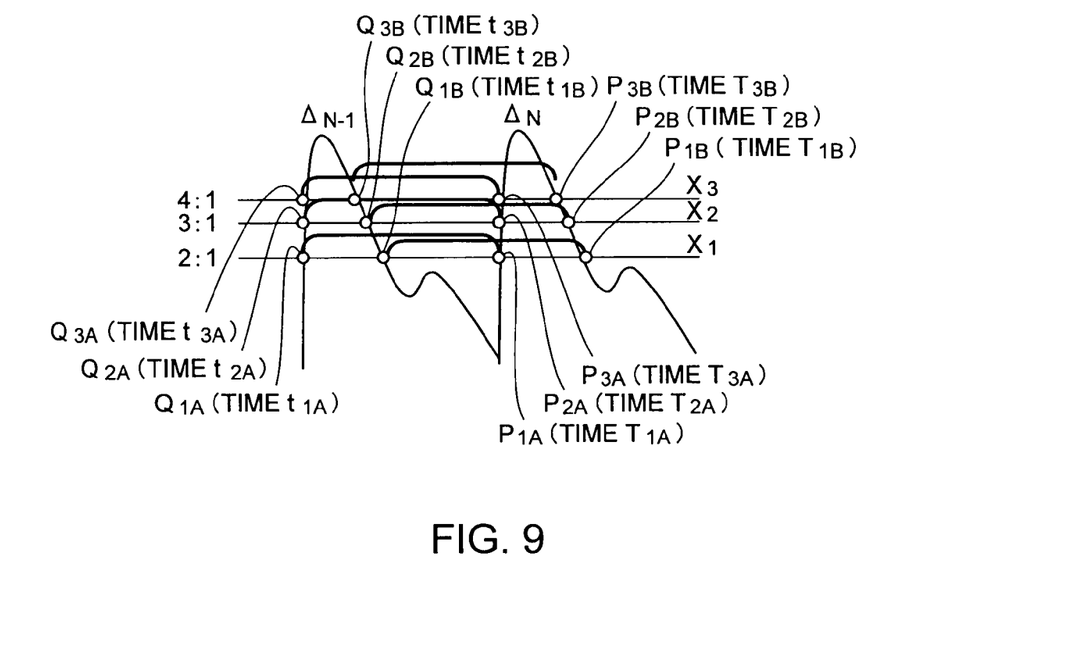
FIG. 9 is a drawing for explaining the pulse wave period calculation process.

Next, the reference value calculating unit 203 calculates one or more reference values between the maximum value and the minimum value in the predetermined period (S103). Each of the reference values corresponds to an internally dividing point between the maximum value and the minimum value. FIG. 8 shows an internally dividing point "X" between the maximum value "M" and the minimum value "m". The internally dividing ratio of the internally dividing point "X" is 3:1. When the internally dividing ratio of the internally dividing point "X" is expressed by (X−m)/(M−m), the internally dividing ratio of the internally dividing point "X" is expressed as 0.75. When calculating one or more internally dividing points, the reference value calculating unit 203 calculates the difference between the maximum value and the minimum value as amplitude, and calculates one or more internally dividing points of the amplitude. FIG. 9 shows three internally dividing points $X_1$ (internally dividing ratio is 2:1), $X_2$ (internally dividing ratio is 3:1), and $X_3$ (internally dividing ratio is 4:1).

The analysis unit 116 performs the steps of S102 and S103 for plural periods of the pulse wave. FIG. 8 shows plural periods $\Delta_N$, $\Delta_{N+1}$, $\Delta_{N+2}$, $\Delta_{N+3}$ and internally dividing points in these periods. The periods $\Delta_{N+1}$, $\Delta_{N+2}$, $\Delta_{N+3}$ are predetermined periods other than the period $\Delta_N$. In this embodiment, each of the periods $\Delta_{N+1}$, $\Delta_{N+2}$, $\Delta_{N+3}$ is also an about-one-second period whose center is at its predetermined sampling point. The internally dividing points in the periods $\Delta_N$, $\Delta_{N+1}$, $\Delta_{N+2}$, $\Delta_{N+3}$ have the same internally dividing ratio, 3:1. In this way, the reference value calculating unit 203 calculates the one or more internally dividing points between the maximum value and the minimum value in the predetermined period, based on one or more internally dividing ratios common to plural periods of the pulse wave. FIG. 9 shows internally dividing points $X_1$, $X_2$, and $X_3$ calculated based on the common internally dividing ratios 2:1, 3:1, and 4:1. The analysis unit 116 also performs a step of S104 for plural periods of the pulse wave.

Next, the time calculating unit 204 calculates two or more times in the predetermined period, more specifically, calculates the two or more times at which the pulse wave intersects with the one or more reference values (S104). Each of the calculated times corresponds to the time at an intersection point in the predetermined period, at which the pulse wave intersects with one of the reference values. It should be noted that the intersection point mentioned above need not be a mathematically rigorous intersection point, since the process of FIG. 7 is a numerical calculation. For example, as a time at which the pulse wave intersects with a reference value, the time calculating unit 204 may calculate a time at which the difference between the pulse wave and the reference value is changed from positive to negative or from negative to positive. FIG. 9 shows six intersection points $P_{1A}$, $P_{2A}$, $P_{3A}$, $P_{1B}$, $P_{2B}$, and $P_{3B}$ where the pulse wave intersects with the three reference values $X_1$, $X_2$, and $X_3$. The intersection points $P_{1A}$, $P_{2A}$, and $P_{3A}$ are positive intersection points, i.e., intersection points where the pulse wave having a positive inclination intersects with the reference values. The intersection points $P_{1B}$, $P_{2B}$, and $P_{3B}$ are negative intersection points, i.e., intersection points where the pulse wave having a negative inclination intersects with the reference values. The step of S104 uses the pulse wave data sampled in S101 and the reference values calculated in S103.

FIG. 9 shows the six intersection points where the pulse waveform intersects with the three reference points. The time calculating unit 204 may detect all the six intersection points, or may detect two or more intersection points of the six intersection points. The time calculating unit 204 may detect, for example, only the positive intersection points $P_{1A}$, $P_{2A}$, and $P_{3A}$. This has an advantage of reducing the possibility of incorrectly detecting an intersection point in a small peak area (described later). On the other hand, detecting all intersection points has an advantage of reducing the number of internally dividing points to be calculated and reducing the process load of calculating the internally dividing points. The time calculating unit 204 calculates the time at each detected intersection point. The time calculating unit 204 in this embodiment calculates the times at the six intersection points. FIG. 9 shows the times $T_{1A}$, $T_{2A}$, $T_{3A}$, $T_{1B}$, $T_{2B}$, and $T_{3B}$ at the six intersection points $P_{1A}$, $P_{2A}$, $P_{3A}$, $P_{1B}$, $P_{2B}$, and $P_{3B}$.

Next, the pulse wave period calculating unit 205 calculates a time period between each calculated time in the predetermined period and a corresponding calculated time in a last period before the predetermined period, as a pulse wave period of the pulse wave (S105). Each calculated time period corresponds to a time period between the time at an intersection point in the predetermined period and the time at a corresponding intersection point in the last period before the predetermined period. FIG. 9 shows the predetermined period $\Delta_N$, and the last period $\Delta_{N-1}$, before the predetermined period $\Delta_N$. The period $\Delta_{N-1}$ is older than the period $\Delta_N$. Intersection points $Q_{1A}$, $Q_{2A}$, $Q_{3A}$, $Q_{1B}$, $Q_{2B}$, and $Q_{3B}$ in the period $\Delta_{N-1}$ correspond to the intersection points $P_{1A}$, $P_{2A}$, $P_{3A}$, $P_{1B}$, $P_{2B}$, and $P_{3B}$ in the period $\Delta_N$, respectively. FIG. 9 shows the times $t_{1A}$, $t_{2A}$, $t_{3A}$, $t_{1B}$, $t_{2B}$, and $t_{3B}$ at these corresponding intersection points. The pulse wave period calculating unit 205 calculates time periods $T_{1A}-t_{1A}$, $T_{2A}-t_{2A}$, $T_{3A}-t_{3A}$, $T_{1B}-t_{1B}$, $T_{2B}-t_{2B}$, and $T_{3B}-t_{3B}$, as pulse wave periods of the pulse wave. In this way, the pulse wave period calculating unit 205 calculates two or more pulse wave periods. The pulse wave period calculating unit 205 in this embodiment calculates six pulse wave periods.

Next, the variation calculating unit 206 calculates a variation of pulse wave periods, for the two or more pulse wave periods calculated between the predetermined period and the last period before the predetermined period (S106). The variation calculating unit 206 in this embodiment calculates the average of the two or more pulse wave periods. Furthermore, the variation calculating unit 206 in this embodiment calculates the standard deviation of the two or more pulse wave periods, as the variation of these pulse wave periods. In this way, the variation calculating unit 206 calculates the average and the standard deviation of pulse wave periods, for the two or more pulse wave periods. The variation calculating unit 206 in this embodiment calculates the average and the standard deviation of pulse wave periods, for the six pulse wave periods.

Next, the stability calculating unit 207 calculates, based on the variation of the pulse wave periods, the stability of measuring the pulse wave periods (S107). If the standard deviation is less than a threshold, the stability calculating unit 207 calculates the measurement is stable. On the other hand, if the standard deviation is equal to or greater than the threshold, the stability calculating unit 207 calculates the measurement is unstable.

The step of S105 calculates pulse wave periods, at plural points on the pulse wave. The step of S106 calculates a variation of pulse wave periods, for the pulse wave periods calculated in 5105. If the pulse wave is completely periodic, the pulse wave periods should not depend on the points, and there should be no variation of the pulse wave periods. Therefore, a small variation of the pulse wave periods implies a high reproducibility (repeatability) of the pulse wave. Therefore, the step of S107 determines whether the measurement of the pulse wave periods in the predetermined period is correct or not, based on whether the variation of the pulse wave periods is small or not.

Next, if the measurement is stable, the pulse wave period outputting unit 208 adopts the median of the two or more pulse wave periods, as a measured value of the pulse wave period of the pulse wave (S108). Instead of the median, the average of the two or more pulse wave periods may be adopted. The pulse wave period outputting unit 208 outputs the adopted average or median, as the measured value of the pulse wave period. Examples of the method of outputting the measured value include displaying the measured value, saving the measured value, sending the measured value to an external device, and the like. The pulse wave period outputting unit 208 in this embodiment saves the adopted pulse wave period data in the storage unit 117, together with the number of body motion occurrences for a minute, and the average pulse wave amplitude for a minute.

As described above, according to this embodiment, the steps of S101 to S107 calculate the stability of the pulse wave measurement. The stability calculation in this embodiment does not need, for example, a process of calculating the correlation value between a reference waveform and an observed waveform. Therefore, the processing load of the stability calculation is relatively small. Accordingly, the stability calculation in this embodiment is effective even for a pulse wave sensor having the control unit 127 with a small-scale arithmetic circuit. For example, the stability calculation in this embodiment can be performed with pulse wave periods for a few pulse beats. According to this embodiment, if plural pulse wave periods can be calculated between a predetermined period and a last period before the predetermined period, the stability calculation in the predetermined period can be performed. Therefore, this embodiment allows the stability calculation to be performed in a relatively short time. The pulse wave period data output in S108 can be used, for example, to calculate an autonomic nervous activity, a sleeping condition, or the like.

Now, the internally dividing points and the internally dividing ratios will be described.

As described above, examples of the internally dividing points and ratios are shown in FIG. 9. FIG. 9 shows an internally dividing point $X_1$ having a ratio 2:1, an internally dividing point $X_2$ having a ratio 3:1, and an internally dividing point $X_3$ having a ratio 4:1. When the internally dividing ratios of the internally dividing points are expressed by $(X-m)/(M-m)$, the internally dividing ratios of the internally dividing points $X_1$, $X_2$, and $X_3$ are expressed as 0.67, 0.75, and 0.80 respectively.

Figure 10:
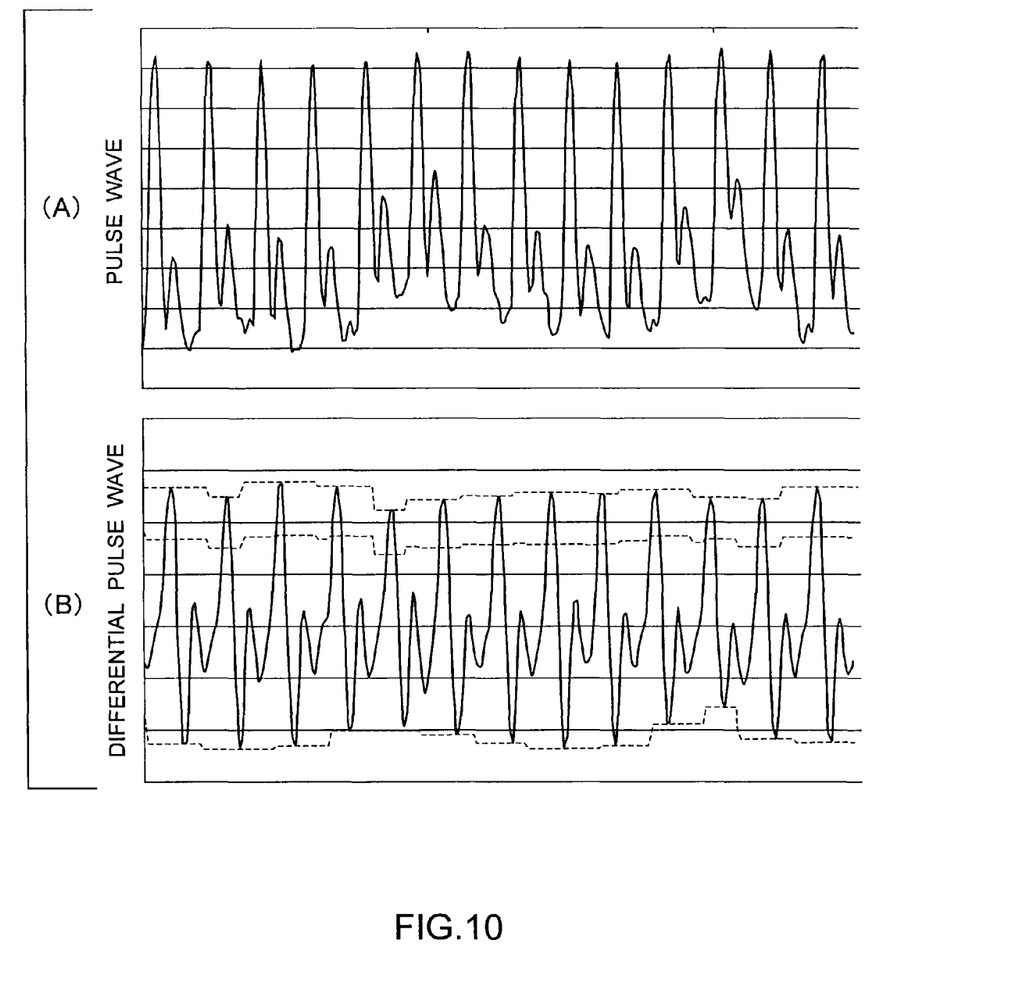
FIG. 10 shows waveforms of a pulse wave and a differential pulse wave.

FIG. 10A shows a waveform of the pulse wave. The waveform changes depending on the conditions of a blood vessel and a blood circulation of the subject, as shown in FIG. 10A. If the subject has strong blood vessel elasticity or the like, the waveform may include a big peak followed by a small peak, as shown in FIG. 10A.

FIG. 10B shows a waveform of a differential pulse wave obtained by differentiating the pulse wave. The differential pulse wave is obtained by detecting the pulse wave and differentiating the detected pulse wave with respect to time. The pulse wave used in the steps of S101 to S108 may be the differential pulse wave shown in FIG. 10B, instead of the pulse wave itself shown in FIG. 10A. In this case, the sampling unit 201 samples the pulse wave data from the differential pulse wave, and the value detecting unit 202 and the time calculating unit 204 use the pulse wave data sampled from the differential pulse wave.

The time differentiation of the pulse wave has an advantage of removing the variation of the baseline of the pulse wave. On the other hand, it has a disadvantage that the small peak may often be emphasized. This is shown in FIG. 10B. Further, it has a disadvantage that the small peak may often come close to the big peak. Therefore, when the time differentiation is performed on the pulse wave, it is necessary to set each internally dividing point above the small peak.

Figure 11:
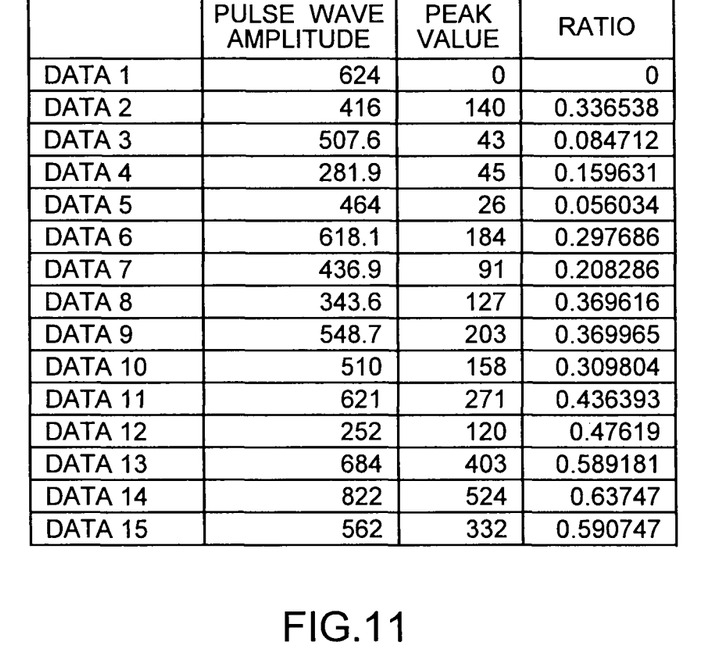
FIG. 11 shows measured results of pulse waves of plural subjects.

FIG. 11 shows measured results obtained by actually measuring pulse waves of plural subjects. The number of the subjects is 15, and the age distribution of the subjects is from 20 to 62. FIG. 11 shows a pulse wave amplitude of a differential pulse wave, and a peak value of a small peak in the differential pulse wave. Further, FIG. 11 shows the ratio of the peak value to the pulse wave amplitude (i.e., the peak value divided by the pulse wave amplitude). In the measured results, the maximum value of the ratios among data 1 to 15 is 0.637 (data 14).

In this embodiment, based on the measured results in FIG. 11, a lower limit of the internally dividing ratios $(=(X-m)/(M-m))$ is set to be a value larger than 0.637. For example, the lower limit of the internally dividing ratios is set to be 0.64, and the internally dividing ratios are set to be 0.64 or larger. This reduces the possibility of incorrectly detecting the small peak in the differential pulse wave. In this embodiment, the lower limit may be set to be 0.65 or 0.70, to secure a larger margin between 0.637 and the lower limit. As described here, the reference value calculating unit 203 sets each internally dividing ratio to be a value equal to or larger than a lower limit which is determined based on measured results of pulse waves of plural subjects. Consequently, each internally dividing ratio can be set to be a value which does not allow to detect the small peak of the pulse wave.

The pulse wave period measuring apparatus 101 may measure, before a normal use by a subject, test data of pulse waves of the subject. In this case, the apparatus 101 can obtain the maximum ratio similar to that of FIG. 11 (0.637) from the test data, and can determine a lower limit of internally dividing ratios based on the obtained maximum ratio. For example, if the maximum ratio is 0.5, the lower limit may be set to be 0.6, to set a margin between the maximum ratio and the lower limit to be 0.1.

Even if a sufficient margin between the maximum ratio and the lower limit is secured like these cases, internally dividing points may be set to be inappropriate values. For example, the positions of the internally dividing points may be shifted, or the settings of the internally dividing points may fail. This is caused by, for example, a distortion or deformation of the pulse wave due to an external disturbance, such as a motion or swing of a living body. In such a case, the pulse wave period measuring apparatus 101 performs a process of deleting a singular value from the internally dividing points. Two examples of such a process will be described.

According to the first example, the variation calculating unit 206 deletes the largest and smallest pulse wave periods, from the two or more pulse wave periods calculated between the predetermined period and the last period before the predetermined period, and calculates the variation of the remaining pulse wave periods. The variation calculating unit 206 repeats this process until the variation of the remaining pulse wave periods reaches a predetermined value. The variation calculating unit 206 in this embodiment repeats the process until the standard deviation of the remaining pulse wave periods reaches less than a predetermined threshold. Each time the process is performed, two pulse wave periods are deleted. If the standard deviation is less than the threshold from the start, this process is not required. Then, the stability calculating unit 207 calculates the stability of measuring the pulse wave periods, based on the number of the pulse wave periods remaining when the variation of the pulse wave periods reaches the predetermined value. In this embodiment, when the number of the pulse wave periods is less than 4, the stability calculating unit 207 calculates that the measurement is unstable.

According to the second example, the variation calculating unit 206 deletes a pulse wave period outside a predetermined range, from the two or more pulse wave periods calculated between the predetermined period and the last period before the predetermined period, and calculates the variation of the remaining pulse wave periods. The predetermined range is determined in advance based on the average and the standard deviation of the pulse wave periods. If there is no pulse wave period outside the predetermined range, this process is not required. Then, the stability calculating unit 207 calculates the stability of measuring the pulse wave periods, based on the variation of the remaining pulse wave periods. The method of calculating the stability is the same as the step of S107.

Hereinafter, a mat sensor 301 in accordance with a second embodiment will be described. The second embodiment is a variation of the first embodiment, and the second embodiment will be described focusing on the differences from the first embodiment.

(Second Embodiment)

Figure 12:
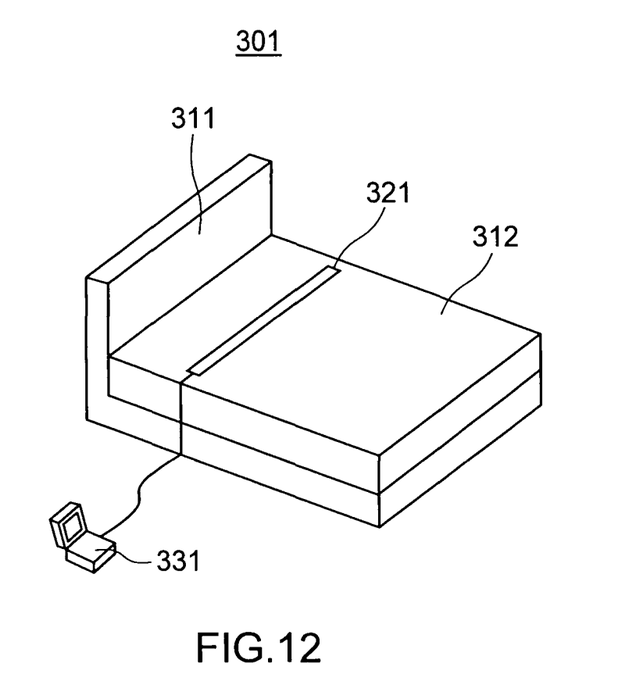
FIG. 12 is an external view of a mat sensor in accordance with a second embodiment.

FIG. 12 is an external view of the mat sensor 301 in accordance with the second embodiment. The first embodiment detects a pulse wave and an acceleration, while the second embodiment detects a heartbeat and a body motion.

The mat sensor 301 includes a bed 311, a mattress 312, a pressure detecting unit 321, and an information processing unit 331. The pressure detecting unit 321 is provided on the surface of the mattress 312, and detects a vibration of the subject's chest or abdomen. This enables the pressure detecting unit 321 to detect the subject's heartbeat and body motion during sleep. Further, the pressure detecting unit 321 can detect whether the subject is in bed or out of bed. The pressure detecting unit 321 in this embodiment includes a piezoelectric device. The piezoelectric device in this embodiment includes a polymer piezoelectric material such as polyvinylidene fluoride formed into a thin film shape, and first and second flexible electrode films attached to first and second sides of the polymer piezoelectric material. The piezoelectric device in this embodiment has a tape-like shape. The information processing unit 331 will be described later.

Figure 13:
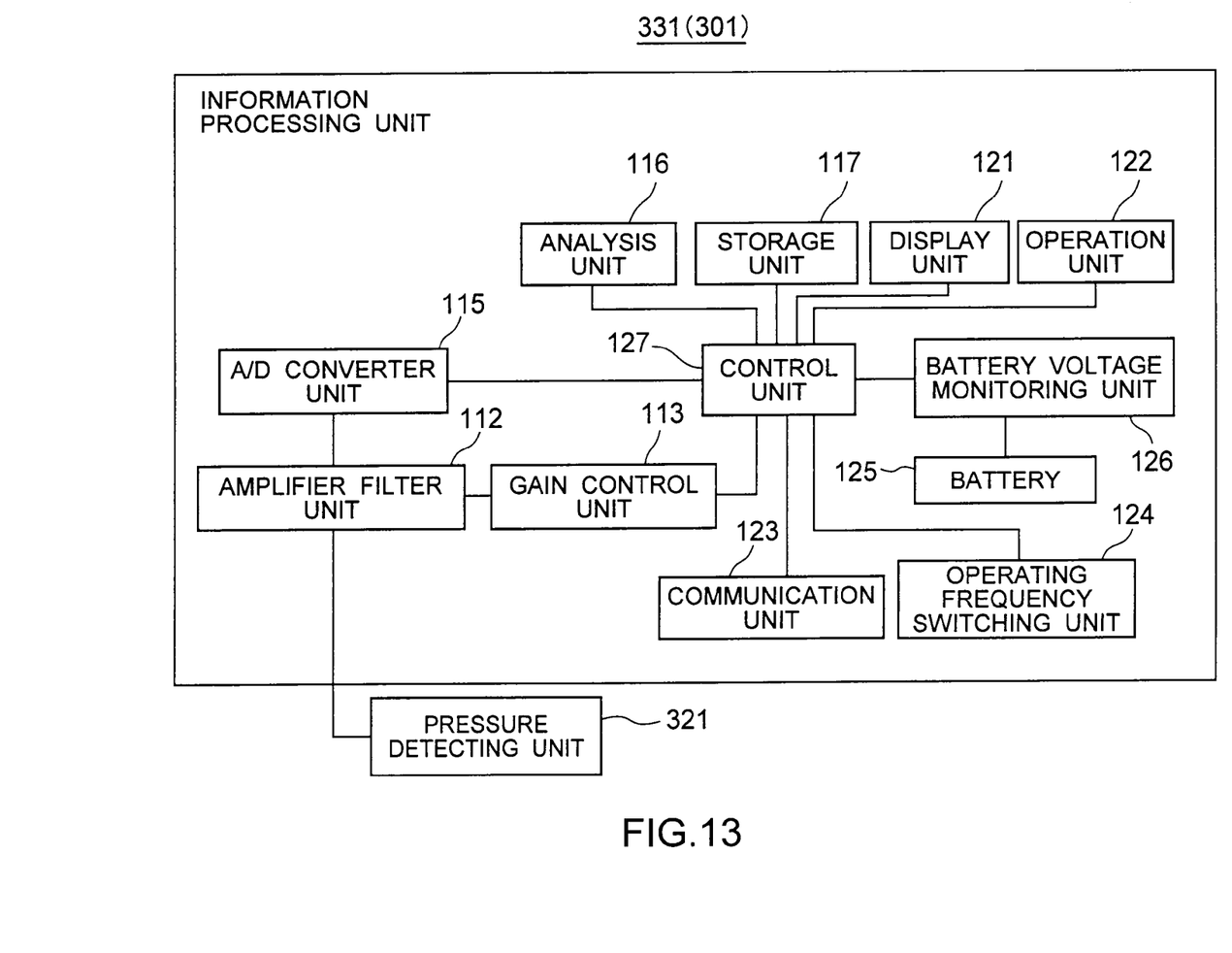
FIG. 13 is a functional block diagram of an information processing unit in FIG. 12.

FIG. 13 is a functional block diagram of the information processing unit 331 in FIG. 12. The information processing unit 331 is connected to the pressure detecting unit 321. The information processing unit 331 is provided with an amplifier filter unit 112, a gain control unit 113, an A/D converter unit 115, an analysis unit 116, a storage unit 117, a display unit 121, an operation unit 122, a communication unit 123, an operating frequency switching unit 124, a battery 125, a battery voltage monitoring unit 126, and a control unit 127.

The information processing unit 331 is different from the pulse wave period measuring apparatus 101 of FIG. 1 in that the information processing unit 331 is not provided with the pulse wave detecting unit 111 and the acceleration detecting unit 114, and in that the amplifier filter unit 112 is connected to the pressure detecting unit 321. Further, the function of the amplifier filter unit 112 in FIG. 13 is different from that of the amplifier filter unit 112 in FIG. 1. The configuration and functions of other functional units in FIG. 13 are the same as those of the corresponding functional units in FIG. 1.

The amplifier filter unit 112 in FIG. 13 is configured to receive an output from the pressure detecting unit 321, separate the output into a body motion component and a heartbeat component, and output the body motion component and the heartbeat component to the A/D converter unit 115. The amplifier filter unit 112 in FIG. 13 includes a filter which is suitable for the frequency band of body motion measurement data, and a filter witch is suitable for the frequency band of heartbeat measurement data.

As described above, the mat sensor 301 detects the subject's heartbeat. The mat sensor 301 performs the same process on a heartbeat detection result as the apparatus 101 in FIG. 1 performs on a pulse wave detection result. The mat sensor 301 can perform a process similar to the pulse wave period calculation process without constraining the subject.

Figure 14:
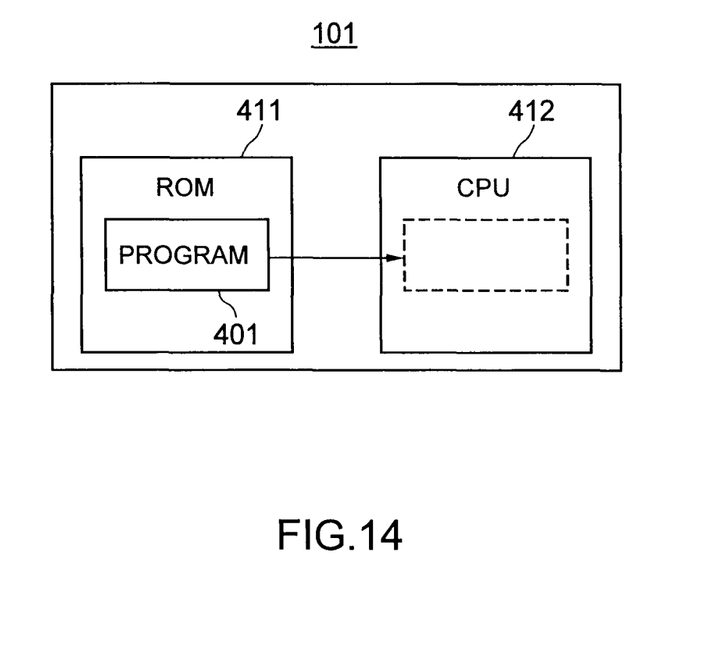
FIG. 14 shows a computer program in accordance with an embodiment of the present invention.

The control of the pulse wave period measuring apparatus 101 of the first embodiment can be performed, for example, by a computer program. A program 401 shown in FIG. 14 is an example of such a computer program. The program 401 in this embodiment is stored in a ROM 411 (e.g., the storage unit 117) of the apparatus 101, and is executed by a CPU 412 (e.g., the control unit 127) of the apparatus 101.

In this case, the control by the control unit 127 in FIG. 1 is realized by the program 401, for example. In this case, the operation of each functional unit in FIG. 1 is controlled by the program 401. Further, the analysis by the analysis unit 116 in FIG. 1 is realized by the program 401. In this case, each functional block in FIG. 6 is realized by the program 401. The program 401 is stored in, for example, a computer readable recording medium such as the ROM 411.

Likewise, the control of the mat sensor 301 of the second embodiment can be performed, for example, by the computer program.

The pulse wave period measuring apparatus in the described embodiment has an advantage that the apparatus can be used in daily life with ease, for example. Furthermore, the apparatus has an advantage that a relatively accurate pulse wave period measurement can be performed in a relatively short time. The configuration of the embodiment is suitable for, for example, a portable pulse wave period measuring apparatus.

The embodiments of the present invention can provide pulse wave period measuring apparatus and method which can calculate the stability of measuring the pulse waves, with a smaller amount of computation for each wavelength. Further, the embodiments of the present invention can provide heartbeat period measuring apparatus and method which can calculate the stability of measuring the heartbeats, with a smaller amount of computation for each wavelength.

The invention claimed is:

1. A pulse wave period measuring apparatus comprising:
a pulse wave detecting unit configured to detect a pulse wave of a subject;
a value detecting unit configured to detect a maximum value and a minimum value in a predetermined period of the pulse wave;
a reference value calculating unit configured to calculate one or more reference values between the maximum value and the minimum value in the predetermined period, based on one or more internally dividing ratios common to plural predetermined periods of the pulse wave;
a time calculating unit configured to calculate two or more times in the predetermined period, the time calculating unit calculating the two or more times at which the pulse wave intersects with the one or more reference values;
a pulse wave period calculating unit configured to calculate a time period between each calculated time in the predetermined period and a corresponding calculated time in a last period before the predetermined period, as a pulse wave period of the pulse wave;
a variation calculating unit configured to calculate a variation of pulse wave periods, for two or more pulse wave periods calculated between the predetermined period and the last period before the predetermined period; and
a stability calculating unit configured to calculate, based on the variation of the pulse wave periods, the stability of measuring the pulse wave periods.

2. The apparatus according to claim 1, wherein,
the reference value calculating unit sets any of the internally dividing ratios $(X-m)/(M-m)$ to be 0.64 or larger, where "M" is the maximum value, "m" is the minimum value, and "X" is any of the reference values.

3. The apparatus according to claim 1, wherein,
the reference value calculating unit sets any of the internally dividing ratios $(X-m)/(M-m)$ to be equal to or larger than a lower limit which is determined based on measured results of pulse waves of plural subjects, where "M" is the maximum value, "m" is the minimum value, and "X" is any of the reference values.

4. The apparatus according to claim 1, wherein,
the reference value calculating unit sets any of the internally dividing ratios $(X-m)/(M-m)$ to be equal to or larger than a lower limit which is determined based on test data of pulse waves of the subject, where "M" is the maximum value, "m" is the minimum value, and "X" is any of the reference values.

5. The apparatus according to claim 1, wherein,
the reference value calculating unit sets any of the internally dividing ratios $(X-m)/(M-m)$ to be a value which does not allow to detect a peak of the pulse wave that should not be detected, where "M" is the maximum value, "m" is the minimum value, and "X" is any of the reference values.

6. The apparatus according to claim 1, wherein,
the pulse wave used by the value detecting unit and the time calculating unit is detected by the value detecting unit and then differentiated with respect to time.

7. The apparatus according to claim 1, wherein,
the time calculating unit calculates, as the two or more times, times at which the pulse wave having a positive inclination intersects with the one or more reference values.

8. The apparatus according to claim 1, wherein,
the time calculating unit calculates, as the two or more times, times at which the pulse wave having a positive inclination intersects with the one or more reference values, and times at which the pulse wave having a negative inclination intersects with the one or more reference values.

9. The apparatus according to claim 1, wherein,
the variation calculating unit calculates, as the variation of the pulse wave periods, the standard deviation of the two or more pulse wave periods.

10. The apparatus according to claim 1, wherein,
the variation calculating unit deletes a singular pulse wave period from the two or more pulse wave periods, and calculates the variation of the remaining pulse wave periods.

11. The apparatus according to claim 1, wherein,
the variation calculating unit repeats a process of deleting the largest and smallest pulse wave periods from the two or more pulse wave periods and calculating the variation of the remaining pulse wave periods, until the variation of the remaining pulse wave periods reaches a predetermined value; and
the stability calculating unit calculates the stability of measuring the pulse wave periods, based on the number of the pulse wave periods remaining when the variation of the pulse wave periods reaches the predetermined value.

12. The apparatus according to claim 1, wherein,
the variation calculating unit deletes a pulse wave period outside a predetermined range from the two or more pulse wave periods, and calculates the variation of the remaining pulse wave periods; and
the stability calculating unit calculates the stability of measuring the pulse wave periods, based on the variation of the remaining pulse wave periods.

13. The apparatus according to claim 1, wherein,
if the variation is smaller than a threshold, the stability calculating unit calculates the measurement is stable; and
if the variation is larger than the threshold, the stability calculating unit calculates the measurement is unstable.

14. The apparatus according to claim 1, further comprising:
a pulse wave period outputting unit configured to output the average or median of the two or more pulse wave periods, as a measured value of the pulse wave period of the pulse wave.

15. A pulse wave period measuring method comprising:
detecting a pulse wave of a subject;
detecting a maximum value and a minimum value in a predetermined period of the pulse wave;
calculating one or more reference values between the maximum value and the minimum value in the predetermined period, based on one or more internally dividing ratios common to plural predetermined periods of the pulse wave;
calculating two or more times in the predetermined period, the method calculating the two or more times at which the pulse wave intersects with the one or more reference values;
calculating a time period between each calculated time in the predetermined period and a corresponding calculated time in a last period before the predetermined period, as a pulse wave period of the pulse wave;
calculating a variation of pulse wave periods, for two or more pulse wave periods calculated between the predetermined period and the last period before the predetermined period; and
calculating, based on the variation of the pulse wave periods, the stability of measuring the pulse wave periods.

16. The method according to claim 15, further comprising:
outputting the average or median of the two or more pulse wave periods, as a measured value of the pulse wave period of the pulse wave.

17. A computer readable recording medium which records a program causing a computer to execute a pulse wave period measuring method, the method comprising:
sampling pulse wave data from a pulse wave of a subject;
detecting a maximum value and a minimum value in a predetermined period of the pulse wave;
calculating one or more reference values between the maximum value and the minimum value in the predetermined period, based on one or more internally dividing ratios common to plural predetermined periods of the pulse wave;
calculating two or more times in the predetermined period, the method calculating the two or more times at which the pulse wave intersects with the one or more reference values;
calculating the time period between each calculated time in the predetermined period and a corresponding calculated time in a last period before the predetermined period, as a pulse wave period of the pulse wave;
calculating a variation of pulse wave periods, for two or more pulse wave periods calculated between the predetermined period and the last period before the predetermined period; and
calculating, based on the variation of the pulse wave periods, the stability of measuring the pulse wave periods.

18. The recording medium according to claim 17, wherein the method further comprises outputting the average or median of the two or more pulse wave periods, as a measured value of the pulse wave period of the pulse wave.

19. A heartbeat period measuring method comprising:
sampling heartbeat data from a heartbeat of a subject;
detecting a maximum value and a minimum value in a predetermined period of the heartbeat;
calculating one or more reference values between the maximum value and the minimum value in the predetermined period, based on one or more internally dividing ratios common to plural predetermined periods of the heartbeat;
calculating two or more times in the predetermined period, the method calculating the two or more times at which the heartbeat intersects with the one or more reference values;
calculating the time period between each calculated time in the predetermined period and a corresponding calculated time in a last period before the predetermined period, as a heartbeat period of the heartbeat;
calculating a variation of heartbeat periods, for two or more heartbeat periods calculated between the predetermined period and the last period before the predetermined period; and
calculating, based on the variation of the heartbeat periods, the stability of measuring the heartbeat periods.

20. The method according to claim 19, further comprising:
outputting the average or median of the two or more heartbeat periods, as a measured value of the heartbeat period of the heartbeat.

* * * * *